(12) United States Patent
Weiss et al.

(10) Patent No.: US 7,180,084 B2
(45) Date of Patent: Feb. 20, 2007

(54) METHOD AND APPARATUS FOR HIGH-THROUGHPUT INSPECTION OF LARGE FLAT PATTERNED MEDIA USING DYNAMICALLY PROGRAMMABLE OPTICAL SPATIAL FILTERING

(75) Inventors: Adam Weiss, Pickering (CA); Afsar Saranli, Toronto (CA); Oleksiy Lopatin, Scarborough (CA); Alexandre Obotnine, Toronto (CA)

(73) Assignee: Photon Dynamics, Inc., San Jose, CA (US)

( * ) Notice: Subject to any disclaimer, the term of this patent is extended or adjusted under 35 U.S.C. 154(b) by 0 days.

(21) Appl. No.: 11/377,080

(22) Filed: Mar. 15, 2006

(65) Prior Publication Data

US 2006/0186361 A1 Aug. 24, 2006

Related U.S. Application Data

(62) Division of application No. 10/396,760, filed on Mar. 24, 2003, now Pat. No. 7,041,998.

(51) Int. Cl.
*G01N 21/86* (2006.01)
*G01N 21/00* (2006.01)
*H01J 3/14* (2006.01)

(52) U.S. Cl. .................. 250/559.4; 250/216; 356/237.4

(58) Field of Classification Search ............. 250/208.1, 250/216, 559.42, 559.4, 550, 559.45, 548, 250/559.3, 221; 349/24, 25, 29; 356/237.4, 356/237.5, 239.3; 359/237.4, 237.5, 239.3; 382/210, 211
See application file for complete search history.

(56) References Cited

U.S. PATENT DOCUMENTS

| | | | |
|---|---|---|---|
| 3,743,423 A * | 7/1973 | Heinz et al. ................. | 356/71 |
| 4,000,949 A | 1/1977 | Watkins | |
| 4,579,455 A | 4/1986 | Levy et al. | |
| 4,805,123 A | 2/1989 | Specht et al. | |
| 4,806,774 A | 2/1989 | Lin et al. | |
| 4,993,837 A * | 2/1991 | Oshida et al. ............... | 356/401 |
| 5,276,498 A * | 1/1994 | Galbraith et al. ........ | 356/237.2 |
| 5,383,056 A | 1/1995 | Nishii et al. | |
| 5,506,676 A | 4/1996 | Hendler et al. | |
| 5,546,181 A * | 8/1996 | Kobayashi et al. ...... | 356/237.5 |
| 5,617,203 A | 4/1997 | Kobayashi et al. | |

(Continued)

OTHER PUBLICATIONS

Watkins, "Inspection of integrated circuit photo masks with intensity spatial filters" *Proceedings of the IEEE*, vol. 57, No. 9, pp. 1634-1639 (Sep. 1969).

*Primary Examiner*—Georgia Epps
*Assistant Examiner*—Pascal M. Bui-Pho
(74) *Attorney, Agent, or Firm*—Townsend and Townsend and Crew LLP

(57) ABSTRACT

In an inspection system for planar objects having periodic structures, programmable optical Fourier filtering in the focal plane of a telecentric lens system is used to directly identify physical phenomena indicative of non-periodic defects. Lens assemblies and a coherent optical source are used to generate and observe a spatial Fourier transform of a periodic structure in the Fourier plane. Optical Fourier filtering (OFF) is performed in the focal plane using an electrically programmable and electrically alignable spatial light modulator. The spatial light modulator with high signal to noise ratio is electrically reconfigurable according to a feedback-driven, filter construction and alignment algorithm. The OFF enhances any non-periodic components present in the Fourier plane and final image plane of the object. A system having a plurality of inspection channels provides high-throughput inspection of objects with small non-periodic defects while maintaining high detection sensitivity.

8 Claims, 10 Drawing Sheets

U.S. PATENT DOCUMENTS

| | | |
|---|---|---|
| 5,627,678 A | 5/1997 | Nishii et al. |
| 5,742,422 A | 4/1998 | Drake |
| 5,822,055 A | 10/1998 | Tsai et al. |
| 5,907,628 A | 5/1999 | Yolles et al. |
| 5,966,212 A | 10/1999 | Hendler et al. |
| 5,970,168 A | 10/1999 | Montesanto et al. |
| 6,046,808 A | 4/2000 | Fateley |
| 6,061,126 A | 5/2000 | Yoshimura et al. |
| 6,084,671 A | 7/2000 | Holcomb |
| 6,128,078 A | 10/2000 | Fateley |
| 6,137,570 A | 10/2000 | Chuang et al. |
| 6,490,393 B1 | 12/2002 | Zhou |
| 2003/0128416 A1 | 7/2003 | Caracci et al. |

* cited by examiner

METHOD AND APPARATUS FOR HIGH-THROUGHPUT INSPECTION OF LARGE FLAT PATTERNED MEDIA USING DYNAMICALLY PROGRAMMABLE OPTICAL SPATIAL FILTERING

CROSS-REFERENCES TO RELATED APPLICATIONS

The present application is a divisional of application Ser. No. 10/396,760, filed Mar. 24, 2003 now U.S. Pat. No. 7,041,998, entitled "Method And Apparatus For High-Throughput Inspection Of Large Flat Patterned Media Using Dynamically Programmable Optical Spatial Filtering", the content of which is incorporated herein by reference in its entirety.

BACKGROUND OF THE INVENTION

This invention relates to the inspection of flat patterned media using optical techniques. More specifically, this invention relates to the automated optical inspection (AOI) of large flat patterned media, such as thin film transistor (TFT) arrays (the main component of liquid crystal flat panel displays (LCD)). Although the invention is applicable to the general case of inspection of any flat, periodically patterned media, it is particularly useful for the high throughput, in-line inspection of TFT arrays at various stages of their production.

During the manufacturing of LCD panels, large clear sheets of thin glass are used as a substrate for the deposition of various layers of materials to form electronic circuits that are intended to function as a plurality of separable, identical display panels. This deposition is usually done in stages, where in each stage, a particular material (such as metal, Indium Tin Oxide (ITO), Silicon, Amorphous Silicon, etc.) is deposited over a previous layer (or upon the bare glass substrate) in adherence to a predetermined pattern. Each stage includes various steps such as deposition, masking, etching, and stripping.

During each of these stages and at various steps within a stage, many production defects may occur, that may have electronic and/or visual implications for the performance of the final LCD product. Such defects include, but are not limited to: circuit shorts, opens, foreign particles, miss-deposition, feature size problems, and over and under etching. The most common defects, shown in FIG. 1, include: metal protrusion 110 into ITO 112, ITO protrusion 114 into metal 116, a so-called mouse bite 118, an open circuit 120, a short 122 in a transistor 124, and a foreign particle 126.

In a specific application domain, such as TFT LCD panel inspection, the article defects subject to detection are small (down to individual micrometers), thus requiring demanding defect detection limits.

However, mere detection of defects is insufficient. Detected defects must also be classified as process defects, i.e. minor imperfections, which do not undermine the performance of the finished product but are an early indication of the array manufacturing process drifting out of optimum conditions; reparable defects, which can be repaired to improve the array production yield; and finally killer defects, which disqualify the TFT array from further use.

In any conventional AOI system, there is always a compromise between a number of critical characteristics, such as the optical scanning resolution, tact time, detection limits, and cost. These characteristics determine the usefulness or type of application of the AOI instrument. Typically, one characteristic can be optimized or improved by compromising another. For example, the AOI system resolution can be increased, resulting in improved detection limits (smaller defects detectable); these improvements would, however, have an adverse effect on the time needed to complete the inspection (tact time) or the system cost. Conversely, for a different type of application, the detection limits can be relaxed (larger defects detectable) by lowering the system resolution, therefore achieving a shorter tact time and reduced system cost.

The inability of the present art to provide high detection sensitivity and tact time matched to the production speed at an acceptable price has imposed on the LCD industry the use of low performance, short tact time systems as in-line instruments. Higher detection sensitivity systems (always requiring long inspection times and incompatible with the production speed) could only be used as off-line instruments, capable of inspecting only selected TFT panels. This method of inspection is often referred to as the sampling mode of operation.

The operating resolution of an AOI system has a direct impact on its cost. For a short tact time, this cost increases almost exponentially with the increase in operating resolution. Therefore, for high-throughput, in-line applications at production speeds, where a short tact time is required, only comparatively lower resolutions have been feasible for the system.

For the application domain of interest, conventional AOI systems use variants of the pattern comparison technique used to detect the presence and location of defects. These methods take advantage of the periodical character of the object under test and directly compare regions spaced by the pattern period or its multiples.

Those skilled in the art may recognize that prior spatial domain image comparison techniques suffer from the pixelation effect, which always degrades the detection limits of the system. The pixelation effect, often interpreted as noise within an image, becomes especially significant in the vicinity of circuit features where rapid transitions of image intensity occur. This leads to false detections or masking of legitimate defects. These effects are highly undesirable since the inspection instruments are expected to have the highest detection sensitivity in the vicinity of TFT array features, such as transistors, data and gate line crossings. Pixelation suppression methods, such as those primarily based on sub-pixel interpolation and approximation techniques, are used as means to partially alleviate these shortcomings. These methods nevertheless fail to satisfy the demands of this particular application domain.

These inherent limitations have led developers to explore the promise of suppressing observable periodic patterns in the optical domain before pixelation is introduced by digitization of the object image for analysis. It is known, for example, that a well understood property of lenses is the ability to form a two dimensional Fourier spectrum of the object in the lens focal plane. The Fourier transformation occurs entirely in the optical domain before any digitization of the signal. This presents the opportunity to filter periodic patterns in the image spectrum in an optical, analog manner.

Optical filtering presupposes the availability of a suitable spatial light modulator (SLM) placed in the lens focal plane to selectively attenuate the intensity profile formed therein to yield an altered (filtered) image in the image plane. The final image would ideally be digitized through an image capture device, such as a Charge Coupled Device (CCD) sensor. In the particular case of a periodically patterned surface as the object to be inspected, the ideal focal plane intensity profile is a well defined grid of intensity peaks. By means of an ideal specialized filter on the focal plane to mask out these peaks, it was expected that the periodic components of the image would be attenuated while preserving non-periodic signal components, such as those caused by defects in the original pattern.

However, the success of this filtering is highly dependent on a number of the properties of the mask placed in the focal plane, including contrast ratio, spatial resolution, optical quality, and the ability to be reprogrammed with high speed. The lack of suitable technology to implement an SLM with the required properties has rendered the optical Fourier filtering principle impractical in the application domain of interest.

AOI equipment has been characterized by a variety of problems. Most of the implemented solutions are based on spatial domain pattern comparison techniques often used in combination with sensor-level pixel or sub-pixel precision alignment techniques.

U.S. Pat. No. 4,579,455 to Levy et al. describes an alignment and pattern comparison technique where a pair of 7×7 windows are considered on the test and reference images and a squared sum of errors over a multitude of possible 3×3 sub-windows within this window are computed. If the minimum error over these twenty-five combinations exceeds a threshold value, a defect is assumed. The method appears to be capable of compensating for alignment mismatch down to a sensor pixel level.

Arguing about the coarse alignment precision of the method by Levy et al., U.S. Pat. No. 4,805,123 to Specht et al. describes an improved alignment and comparison technique for the detection of defects. In this technique, large windows in test and reference images are used to compute a sensor pixel level correlation between a test image and a reference image. The resulting sampled correlation surface's minimum point is found and a quadratic function is fit to the surface in the neighborhood of this minimum point. Using the fitted quadratic function, a sub-pixel precision translation is obtained to align the test and reference images. The aligned images are compared by thresholding image differences on 2×2 sub-windows on the test and aligned reference images.

Variations and improvements on these basic techniques have also been proposed. For example, U.S. Pat. No. 5,907,628 to Yolles et al., among other things, points out the drawbacks of using the sampled correlation surface to find the minimum and argues that due to a coarse sampling of the surface this point may not correspond to the true minimum. Hence, they argue that the subsequent sub-pixel interpolation step would do little to improve the detected minimum and a false alignment would result, leading to false alarms in detection. Yolles et al. proposes to alleviate these problems by an elaborate comparison process based on improved comparison entities.

Although pattern comparison based instruments have been successfully used in the industry for certain applications, the compromise between the system speed (tact time) and accuracy (defect detection limits) has been a dominant factor imposing what has been considered fundamental limitations. This ever present compromise for conventional inspection methods limits the usefulness of these systems in the application domain of high-throughput, in-line inspection of large flat patterned media at production speeds, where there is concurrent demand for speed and detection sensitivity.

The so called Optical Fourier Filtering (OFF) (also known as Fourier Spatial Filtering) is a known and understood technique. The attempts to use OFF for repetitive patterned surface defect detection dates back to a paper by Watkins entitled "Inspection of integrated circuit photo masks with intensity spatial filters," published in *Proceedings of the IEEE* vol. 57, No 9, (September 1969), wherein the properties of such spatial filters are described. This was followed by the invention reported in U.S. Pat. No. 4,000,949 to Watkins et al describing fundamental aspects of basic OFF for patterned surface inspection.

As the technology to implement Fourier spatial filters proved feasible in certain application areas, a number of contributions followed. These include, for example, U.S. Pat. No. 4,806,774 to Lin et al., where a basic bright field illumination Fourier spatial filtering setup is described for microcircuit die inspection, and U.S. Pat. No. 5,383,056 and No. 5,627,678 both to Nishii et al., where particular lens arrangements with favorable properties are described. In U.S. Pat. No. 5,276,498 to Galbraith et al., another application of the Fourier spatial filter to highly periodic semiconductor wafer inspection is presented. The described system is designed for scanning a surface incorporating two regions with different light diffracting patterns. This surface is scanned by a narrow beam of light. The system implements a programmable SLM through the use of two successive stages of light valves, each stage being composed of a one-dimensional array of light valves forming linear stripes and being in transverse configuration to one another.

Another proposed system in U.S. Pat. No. 5,506,676 to Hendler et al considers a spatial separator, such as a micromirror device, to redirect different parts of the lens focal plane information into different light intensity sensors for parallel analysis and The system does not incorporate an image capture device.

Other U.S. patents which disclose relevant art include:

- U.S. Pat. No. 6,490,393 to Zhou, entitled Integrated optical multiplexer and demultiplexer for wavelength division transmission of information;
- U.S. Pat. No. 6,137,570 to Chuang et al. entitled System and method for analyzing topological features on a surface;
- U.S. Pat. No. 6,128,078 to Fateley entitled Radiation filter, spectrometer and imager using a micro-mirror array;
- U.S. Pat. No. 6,084,671 to Holcomb entitled Surface analysis using Gaussian beam profiles;
- U.S. Pat. No. 6,061,126 to Yoshimura et al. entitled Detecting system for surface form of object;
- U.S. Pat. No. 6,046,808 to Fateley entitled Radiation filter, spectrometer and imager using a micro-mirror array;
- U.S. Pat. No. 5,966,212 to Hendler et al. entitled High-speed, high-resolution, large area inspection using multiple optical Fourier transform cells; and
- U.S. Pat. No. 5,822,055 to Tsai et al. entitled Optical inspection of a specimen using multi-channel responses from the specimen using bright and darkfield detection.

Despite their inherent limitations, which cause high false alarm rates or limited sensitivity through relaxed thresholds, conventional pattern matching techniques have remained the dominant inspection techniques throughout the industry. This appears to be due to the nature of the sampling process, which does not attempt to perform 100% inspection at production speeds and does not emphasize the missed defect rate for the inspection system. However, the emerging application domain of high-throughput in-line optical inspection at production speeds imposes tighter speed and accuracy constraints, which are not achievable by such conventional systems at a practical cost.

Although OFF has been considered to be a candidate to achieve both speed and detection accuracy concurrently, its application has not been considered practical due to a range of problems. As the size and contrast of the target defects to be detected diminishes, the accuracy, optical quality, and contrast of the masking pattern used as the optical filter becomes crucial. Achieving this type of quality in the past has been impossible except through the use of either static masks (such as photographic films or holographic gratings) or through static or difficult-to-configure mechanical systems. Static masks remain unsuitable for the presently considered application domain, since the pattern on the material to be inspected often needs to be changed during the regular operation of an AOI instrument and static masks cannot be quickly reconfigured to inspect the object with the new pattern or compensate for the varying orientation of the same pattern.

Re-configurable mechanical systems such as the ones described in U.S. Pat. No. 5,742,422 to Drake and U.S. Pat. No. 5,970,168 to Montesanto et al. attempt to partially solve this problem while preserving optical quality. However, the resulting systems are unacceptably slow to reconfigure. Moreover, they are constrained with respect to the realizable masking patterns, usually limited to a restricted number of horizontal and vertical lines. The use of lines as the masking pattern also causes its own adverse effects, manifesting as parasitic ghosts of defects in the filtered images. Furthermore, the mechanical implementations of the Fourier filters are complex, costly, unreliable, and unacceptably large in size and, therefore, cannot be easily expanded. For example, it is desirable to provide for multiple parallel inspections of a large surface area within tight tact time requirements.

Electrically programmable SLM devices first emerged in the last decade, at first showing some promise in solving the high speed filter reconfiguration problem. However, the available devices, such as light valves and early forms of transmissive LCDs, could not meet desired performance specifications. These requirements include:

High contrast ratio and high optical quality (transparency/reflectivity and optical uniformity), to achieve very high spectral suppression and undistorted signal transmission, leading to desired detection limits;

High spatial resolution and small size, to be feasible within compact optical arrangements and thus make multiple channel operation realizable;

A large fill-factor to minimize mask surface effects (having the structure of a grid) which causes undesired parasitic diffraction patterns on the filtered image; and Operability within a large range of incidence angles, required by large Field of View (FOV) optical channel arrangements, enabling the coverage of a larger inspection surface area with a smaller number of inspection channels.

Therefore, these devices were not practical for use in the high-throughput, in-line optical inspection of large flat patterned media at production speeds, while also satisfying industry requirements for detection limits. Thus, the promise was unfulfilled.

SUMMARY OF THE INVENTION

According to the invention, in an inspection system particularly for inspection of planar structures, the optical Fourier filtering (OFF) principle is employed in conjunction with an electrically-programmable and electrically-realignable high-resolution, high-fill factor, high-contrast, high-uniformity, high-light throughput spatial light modulator (SLM) as a programmable Fourier mask. An image of the object to be tested is projected (by illumination using appropriate spatially coherent optical energy or the like) through a first lens assembly onto the Fourier plane at which is located an electrically programmable and electrically realignable Fourier mask or reflective element in the form of s spatial light modulator (SLM). The inverse Fourier transform is projected through a second lens assembly onto the final image plane. The SLM is programmed to invoke a single center spot on the SLM of a size appropriate to the center spot of the Fourier image, and the SLM spot is scanned around the center of the Fourier image to electrically center the SLM blocking pattern with respect to the incident Fourier image by using image intensity feedback from the optical signal as detected at the final image plane. Then the SLM is programmed to invoke an accurate rotationally alignable mask, such as a cross-hair set, centered with respect to the image. The cross-hair set or the like masks any optical radiation in alignment with the cross-hair set. The SLM pattern is then electrically rotated to rotationally align the SLM cross-hair pattern with the periodic pattern of the Fourier image by using image intensity feedback from the optical signal detected at the final image plane. Thereafter, the SLM is programmed to electrically scan and sample the Fourier image detecting, at the final image plane, the intensity profile for every element or line of elements of the Fourier image in accordance with the previously-determined alignment information. For inspection of an object to be tested, the reconstructed Fourier image intensity profile is programmed into the SLM as a mask of the periodic elements so that the Fourier image incident at the Fourier plane at which the SLM is located is masked and the position of non-periodic components, typically defects, are highlighted in the image projected on the final image plane.

Commercially available high resolution LCD spatial light modulators are employed for the first time in a system according to the invention.

The present invention specifically addresses the problem of optically inspecting large flat patterned media, such as high density TFT-LCD panels for production defects, in a high-throughput in-line mode of operation at production speeds, with target defect detection limits equaling systems operating at much slower speeds.

The present invention makes it possible to meet the required tact time and detection limit requirements concurrently by means of a system which has a considerably lower resolution than an equivalently sensitive conventional AOI instrument. In the present invention, lower resolution provides the speed required to meet the tact time while a plurality of parallel OFF inspection channels provides the detection sensitivity to meet the demanding defect detection limits.

The invention will be better understood by reference to the following detailed description in connection with the accompanying drawings.

DESCRIPTION OF SPECIFIC EMBODIMENTS OF THE INVENTION

Figure 1:
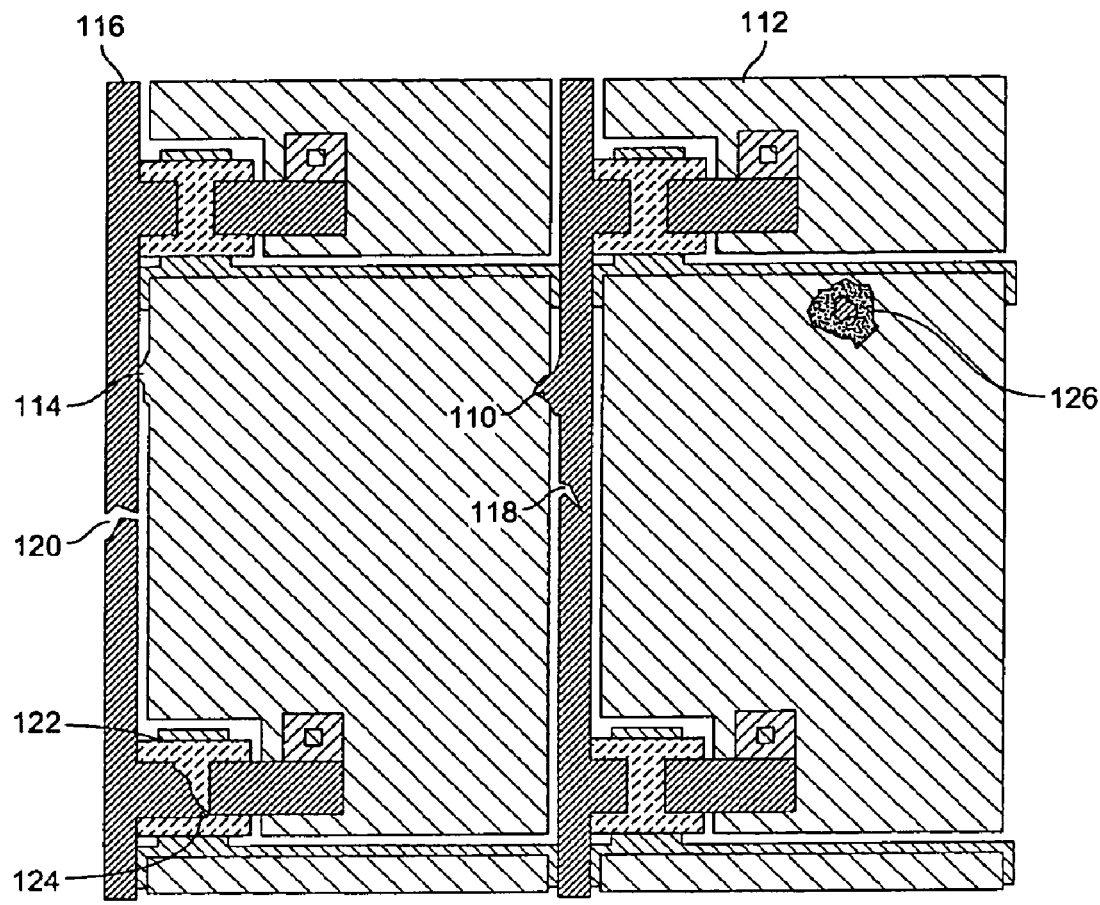
FIG. 1 is a top view of a portion of a large flat patterned medium with periodic transistor arrays under construction for illustrating possible non-periodic defects.
Figure 2:
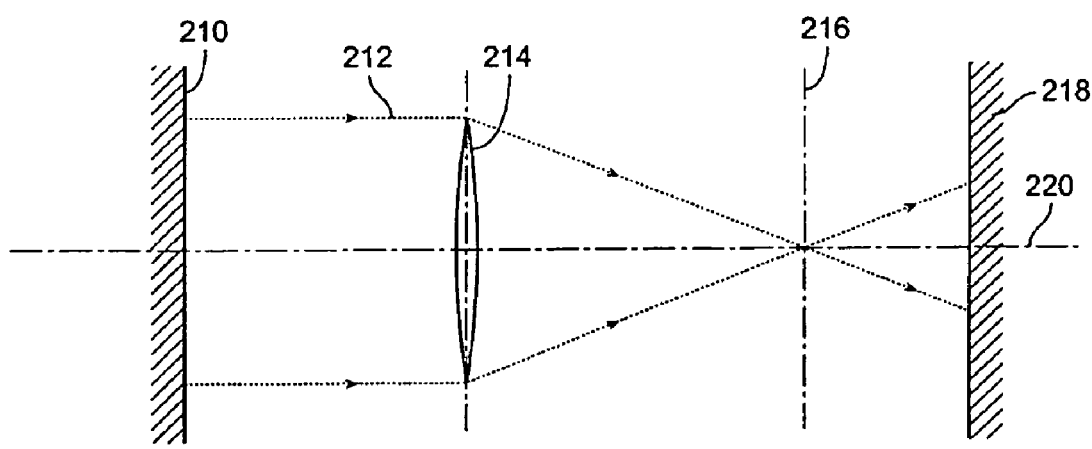
FIG. 2 is a schematic diagram of a lens system illustrating a Fourier plane.

FIG. 2 illustrates the general arrangement of a lens system illustrating optical Fourier transformation. When a periodically patterned surface, located in the object plane 210 of the lens system, is illuminated by collimated, spatially coherent light, it acts as a diffraction grating. The diffracted light 212 is integrated by the lens module 214 and an interferogram of the periodical structure is formed in the lens focal plane 216. This interferogram later results in an image of the object plane after light reaches the image plane 218. It is known that the interference pattern observed in the lens focal plane corresponds to the optical Fourier transform of the object plane. Due to this physical property, the lens focal plane is also referred as the Fourier plane. The size of the Fourier plane and thus the spatial frequency scale within the Fourier plane is determined by the design parameters of the first lens module and the wavelength of the illuminating light.

Figure 3A:
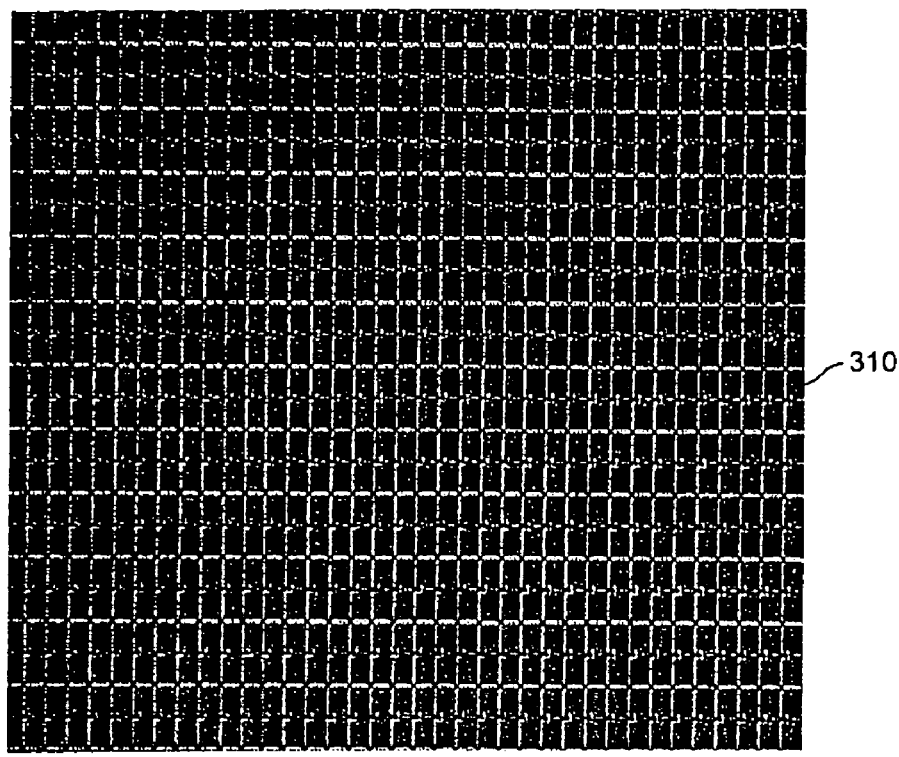
FIG. 3A is a photographic image of a TFT LCD array.
Figure 3B:
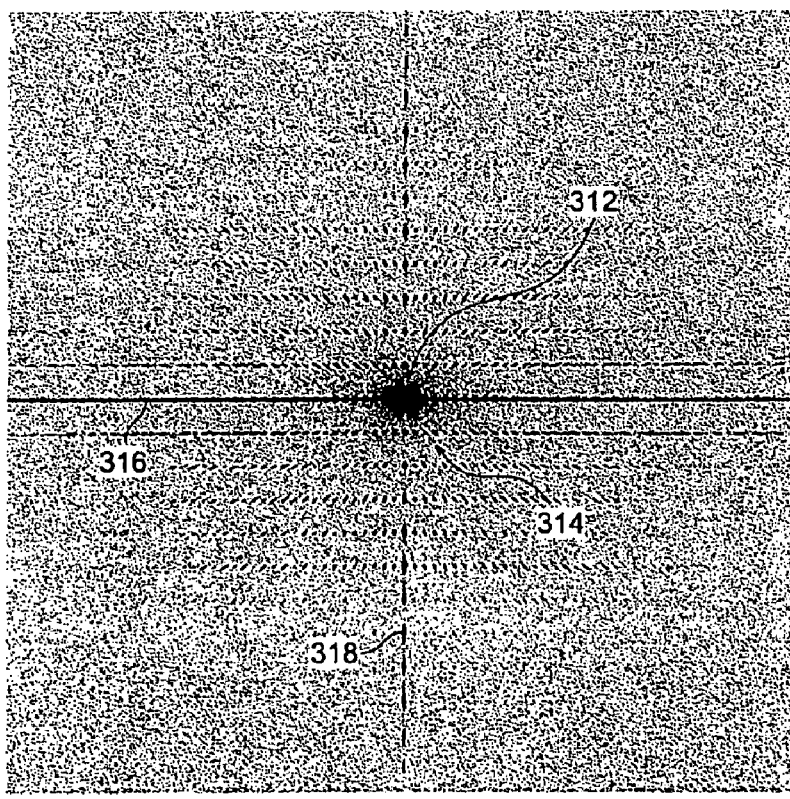
FIG. 3B is a photographic reconstruction of a Fourier plane image.

FIG. 3 illustrates this property. FIG. 3A is an actual image of a TFT LCD array with a substantially periodic structure and 310 is a single cell. FIG. 3B illustrates the digitally captured image of the lens focal plane interferogram where 316 and 318 are the primary axes of periodicity. The central peak 312 corresponds to the uniform gray level component (DC), located at the exact center point of the pattern, as well as the low frequency unevenness due to illumination and sample reflectivity. The remaining peaks 314 correspond to the periodic components in the signal.

Masking (attenuating) selected regions of the interferogram comprises OFF and achieves the desired filtering effect in the final image. For periodic pattern inspection, this takes the form of masking the components of the interferogram 314 corresponding to the periodicity of the original signal while preserving transparency for the rest of the focal plane. This operation would suppress the energy of the periodic signal components while passing the signal energy corresponding to non-periodic components, which are identified as defects.

Figure 4A:
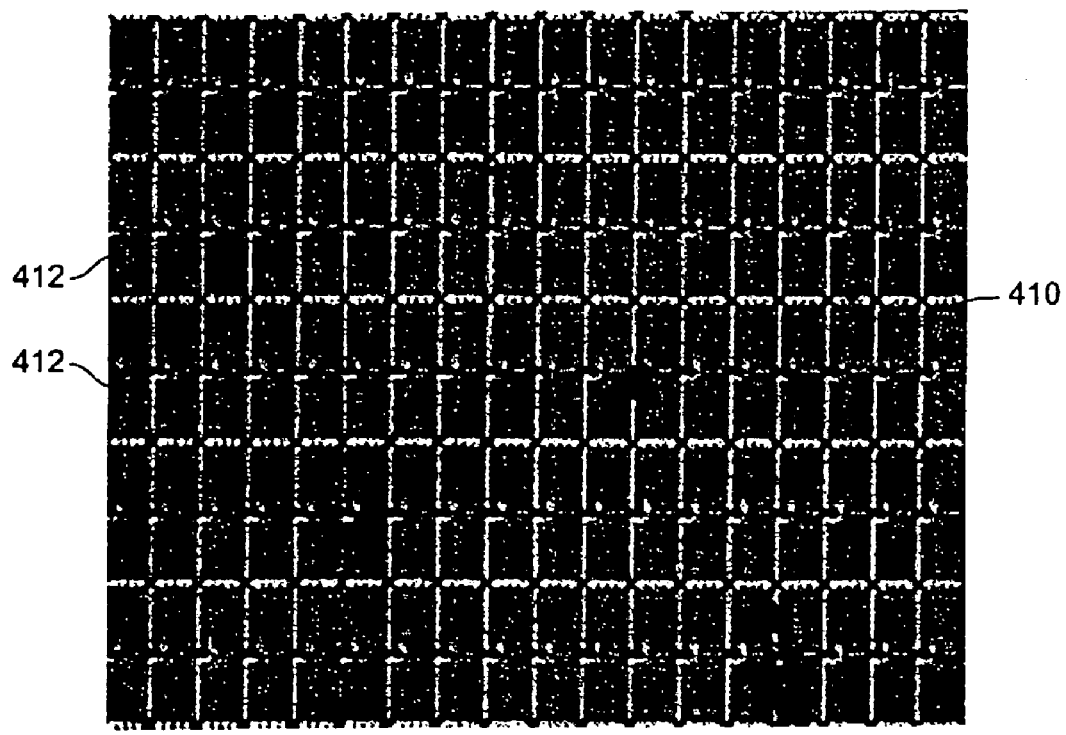
FIG. 4A is a photographic image of a region of an LCD lattice with defects and a marker.
Figure 4B:
FIG. 4B is a photographic reconstruction of the image plane image that has been filtered, revealing defects due to lack of periodicity.

FIGS. 4A–4D illustrate the Fourier filtering operation. In FIG. 4A, a region of the LCD lattice with larger 412 and smaller 410 defects is illustrated. In FIG. 4B, the same lattice section filtered with a proper optical mask is illustrated and a marker optical fiber 414 is clearly visible.

Figure 4C:
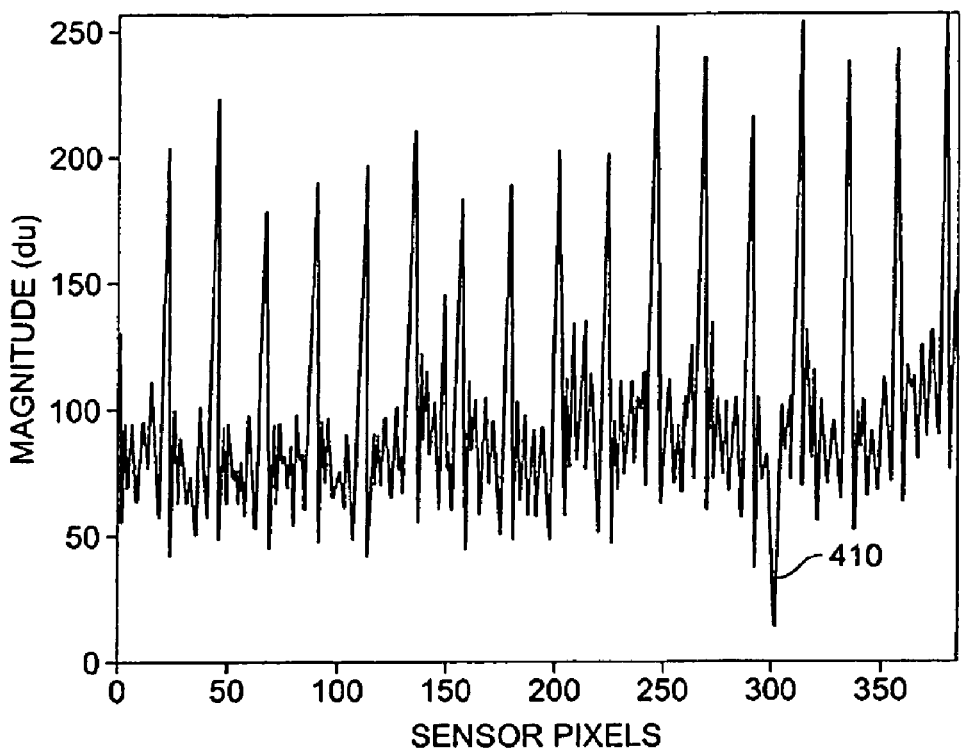
FIG. 4C is a cross-sectional view of a low contrast "dark" defect as seen in FIGS. 4A and 4B.
Figure 4D:
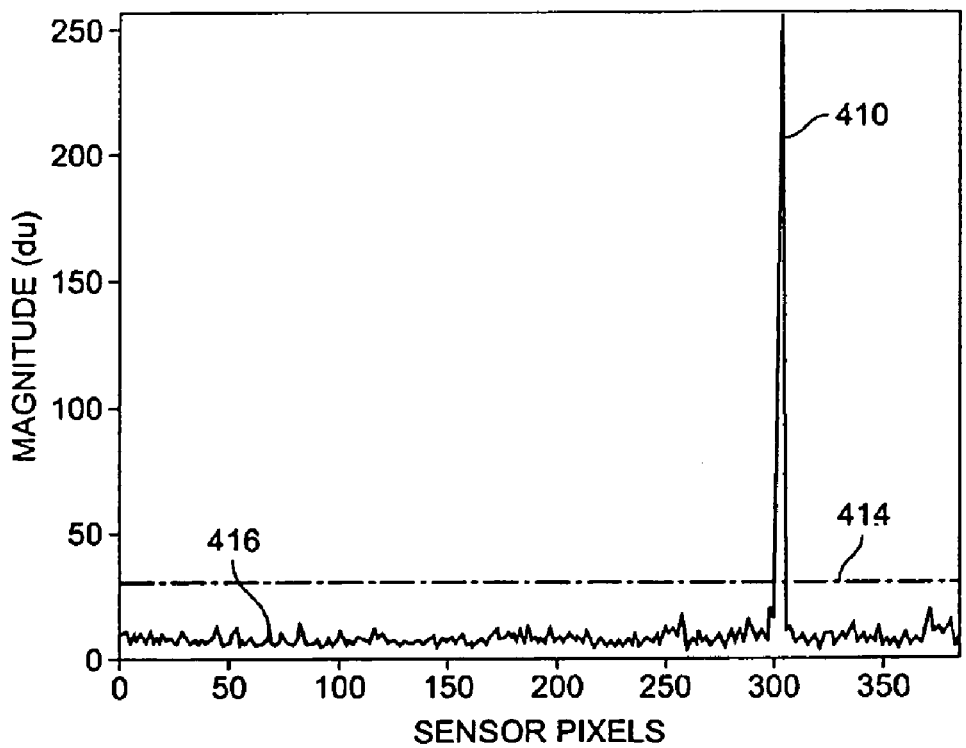
FIG. 4D is a cross-sectional view of a low contrast "dark" defect as seen in FIGS. 4A and 4B.

FIGS. 4C and 4D illustrate cross sectional views of a low contrast "dark" defect 410. The defect contrast is significantly improved and the filtered defect signal rises over the uniformly low background 416. Since the optical Fourier filter has also eliminated the low spatial frequency background, a simple fixed threshold 414 is sufficient to perform defect detection. It can be observed that the periodic lattice is close to the camera noise level while the defects are clearly observable with distinguished signal-to-noise ratio (SNR).

An embodiment of the present invention targets the high-throughput, in-line inspection of large area flat patterned media such as high resolution TFT LCD panels at production speeds. A significant benefit provided by the present invention is the ability to meet detection limits substantially exceeding the system's optical and image capture resolution through innovative use of OFF. This results in a system which can equal the detection limits of slower, higher resolution conventional systems while achieving a scanning speed not realizable by such conventional systems.

Specifically, we have developed an AOI system which can detect low contrast defects only 20 digital units (DU) above the surrounding background (out of 256 DU for an 8-bit camera), of 3 µm equivalent size, with an optical and electronic system designed for 7.6 µm object plane resolution. The detection limit is improved to 2 µm equivalent defect size for medium contrast (~100 DU above background) defects. These results are equally valid for defects which are adjacent to or within periodic features of the lattice including the transistors.

The high speed required to meet the demanding tact time is achieved through reduced system resolution, along with very simple and fast threshold-based digital processing, combined with a large FOV optics design. The system uses multiple identical imaging channels, each equipped with large FOV optics, to cover the entire inspection surface on multiple bi-directional inspection passes.

To meet the same demanding detection limits with the reduced system resolution and simple digital signal processing, the invention uses OFF in combination with a high resolution electrically programmable Liquid Crystal on Silicon (LCOS) SLM in the lens focal plane. The periodic components in the signal are suppressed down to camera noise level while illumination intensity is boosted to a level that would normally cause camera saturation. A very high defect SNR is thus achieved. To achieve this high SNR required by the subsequent detection stage, the SLM has to meet strict specifications as herein described.

Figure 5A:
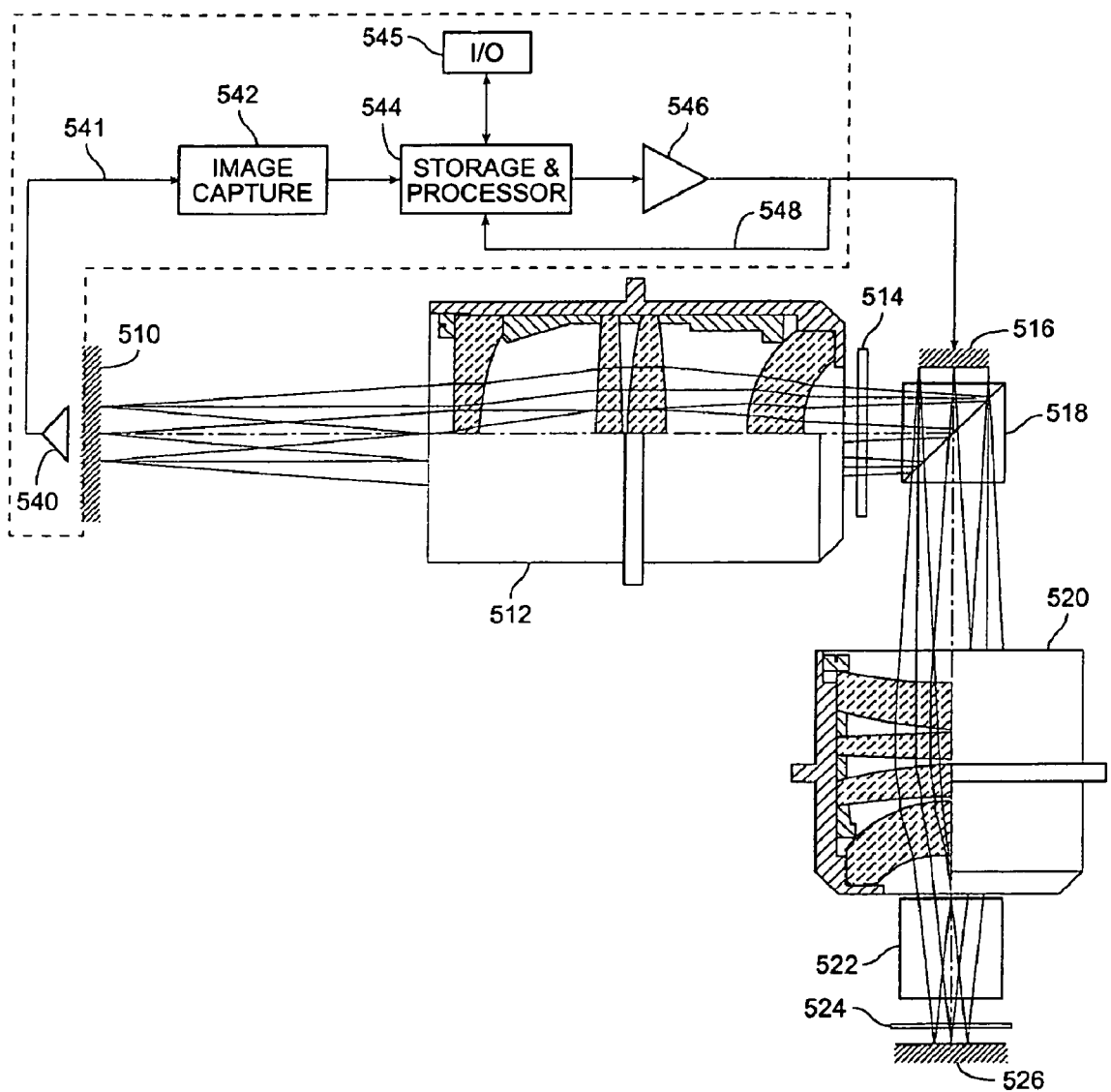
FIG. 5A is a ray tracing diagram of a reflection mode device according to the invention.
Figure 5B:
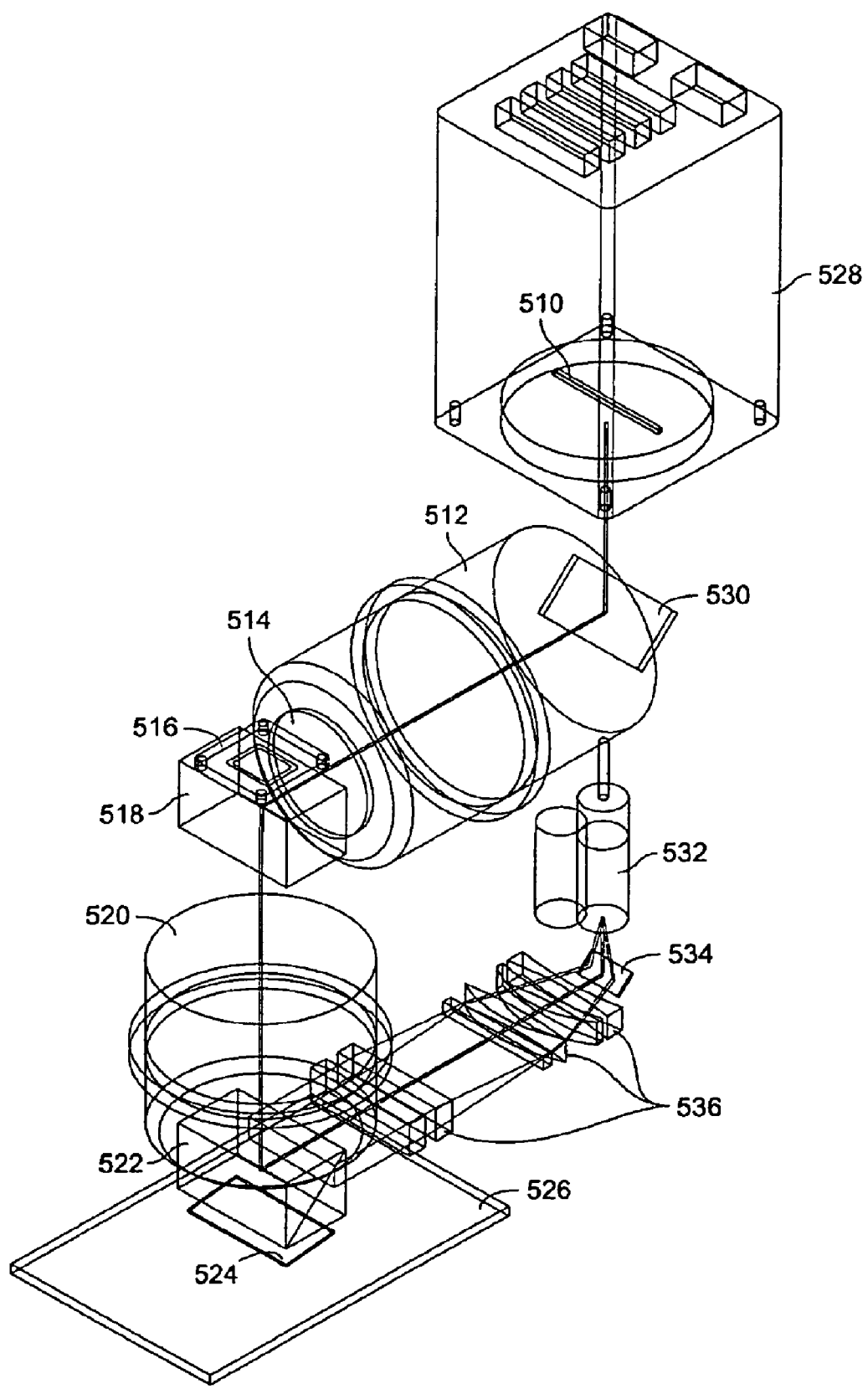
FIG. 5B is a schematic diagram of the reflection mode device according to the invention.

FIG. 5A illustrates the telecentric lens design and optical arrangement for OFF which comprises an embodiment of the present invention. FIG. 5B illustrates the illuminator arrangement and the image capture device.

Referring to FIG. 5A, collimated, spatially coherent light generated using a semiconductor laser 532 and collimating optics 536 enters the optical path through a beam splitter 522 and a ¼ λ retardation wave-plate 524 to illuminate the area being inspected 526. The light reflected from the surface of the area being inspected passes through a first lens assembly 520 and another beam splitter 518, which is disposed adjacent to an electrically controllable reflective SLM device 516. The SLM device 516 is placed in the focal plane of the first lens system. The light reflected from the SLM device 516, which is filtered by the masking pattern downloaded to the SLM, is reflected by the beam splitter 518 and passes through a polarizer 514 and a second lens assembly 512 and is projected onto the final image plane 510. In the final image plane 510, a detector 540 provides a feedback signal 541 to the electrically controllable SLM 516 through a feedback network comprising a detector 540, an image capture device 542, a storage and processing device 544, an input/output (I/O) device 545, and an electronic servo control 546. In particular embodiments, the detector 540 and image capture device 542 may be combined into a single CCD image capture device. Moreover, additional feedback loops 548 may be utilized. As will be described with reference to FIG. 6, below, the SLM 516 and the feedback network are used in an interactive fashion to determine and optimize the SLM filtering pattern, including electrical centering and rotational alignment of the SLM 516.

The lens system is designed for 7.6 μm object plane resolution. The first lens has a focal length of 80 mm and the compound optical system composed of the first and second lenses has an f-number of 4.0. The detailed specifications of the lens system are given in Table 1, below. In this particular lens design, which is composed of two groups, the first group 520 is optimized to produce the required optical resolution (small spot size and minimal aberrations) in the lens focal plane and the compound first 520 and second group 512 of lenses are optimized to provide optical resolution matching the image detector resolution in the image plane 510.

The lens system design is telecentric in order to maintain a consistent spatial frequency spectrum throughout the entire FOV and consequently uniform defect detection limits throughout the entire FOV.

As shown in FIG. 5B, another feature of the present invention is that a Time-Delay Integration (TDI) line scan CCD sensor 528 capable of bi-directional operation may be used. The TDI CCD sensor provides for increased light sensitivity, while the bi-directional property of the image sensor facilitates bi-directional imaging scans of the surface being inspected.

One embodiment of the present invention employs a collimated, spatially coherent light source in reflective bright field mode. Due to the use of a line scan CCD sensor, the illuminator is designed for an elliptical field of illumination over the surface being inspected. The light intensity profile is uniform along the long axis of the ellipse. Sizes of the illuminated area are selected to provide the required FOV and localization of light intensity peaks in the Fourier plane. This is achieved by means of a beam path folding mirror 534, a collimator lens arrangement 536 and a single-mode semiconductor laser 532 producing 30–50 mW of output power. The illumination wavelength is optimized at 660 nm (red) to provide the best contrast compromise between various TFT array materials.

The present invention takes advantage of light polarization control to prevent illumination losses resulting from the two beam splitters present in one embodiment of device operation. This is achieved by means of a ¼ λ retardation wave-plate 524 and two polarizing beam splitters 516 and 522. The complementary polarizer 514 is used as a clean-up element. This method reduces illumination losses by ~16 times for this type of two beam splitter arrangement and renders the imaging task feasible with a commercially available single-mode semiconductor laser.

TABLE 1

| | |
|---|---|
| Object plane | 31 mm Ø |
| Fourier plane | 20 mm Ø |
| Input beam | Collimated, uniform illumination |
| Maximum FOV | ±7.13° |
| EFL | 80.0 mm |
| Fourier plane f-number | 2.58 |
| Wavelength | 660 nm |
| Object to first lens vertex* | 50 mm |
| Last lens vertex to Fourier plane | 89.4 mm |
| First to last vertex length | 48.2 mm |
| Fourier plane spot size | 4.5, 4.4, 7.2, and 12.9 μm rms |
| Input plane wave angles for SS | (0°, 2.2°, 5.1°, and 7.13°) |
| Predicted Fourier plane SS for tolerances | 9.1, 9.6, 13.7, and 20.0 μm rms |
| Barrel Ø | 77.8 mm |
| Barrel length | 85.7 mm |
| Element cosmetics | 60/40 scratch/dig |
| AR coating | λ/4 MgF$_2$(Max R < 0.5%) |
| Estimated transmission | ~94% |
| Proposed test | Spot size or MTF |

TABLE 2

| | |
|---|---|
| Object plane | 31 mm Ø |
| Fourier plane | 20 mm Ø |
| Image plane | 53.8 mm Ø |
| Input beam | f/4.0, telecentric |
| Magnification | 1.72× |
| Inverse transform lens EFL | 141.5 mm |
| Wavelength | 660 nm |
| Fourier plane to first inverse lens vertex | 60 mm |
| Last inverse lens vertex to image plane | 109 mm |
| Inverse lens first to last vertex length | 95 mm |
| Inverse lens barrel Ø | 82.0 mm |
| Inverse lens barrel length | 113.6 mm |
| Nominal MTF performance at 38.5 LP/mm | 74%, 75%, 72% and 71% |
| Input object field points | (0, 5.7, 12.1, 15.5 mm) |
| Predicted MTF performance at 38.5 LP/mm with tolerances (assumes worst meridian TAN values) | 50%, 55%, 56% and 34% |
| Element cosmetics | 60/40 scratch/dig |
| AR coating | λ/4 MgF$_2$ (Max R < 1.5%) |
| Estimated Fourier inverse lens transmission | ~92% |
| Proposed test | Spot size or MTF |

Figure 5C:
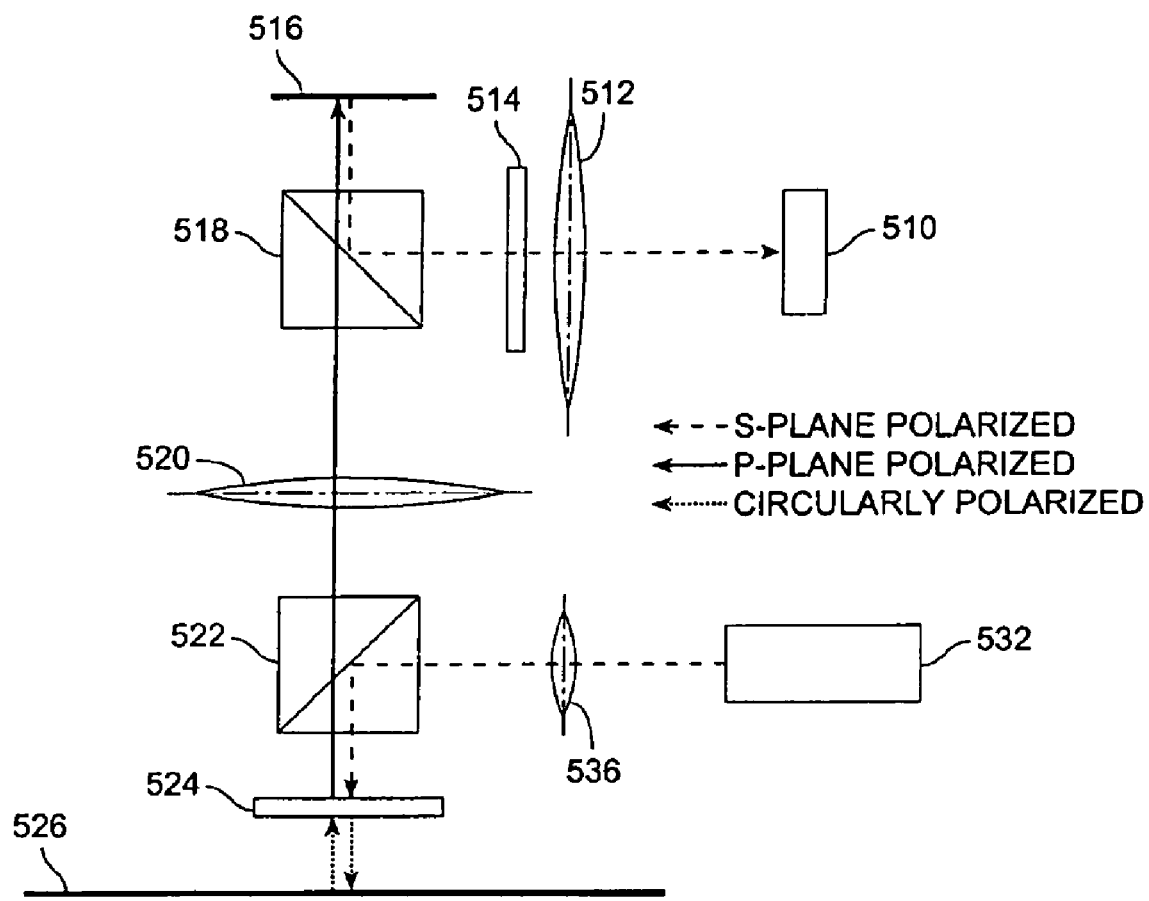
FIG. 5C is a schematic diagram of a reflective mode device employing polarized light.

The detailed operation of this polarization control scheme is illustrated in FIG. 5C. An S-plane polarized coherent beam from a laser is fed to the first beam splitter 522, where almost total reflection is obtained. Then the reflected beam passes through a ¼ λ retardation wave-plate 524, where it is converted into a circularly polarized beam. When the circularly polarized beam is reflected from the inspected surface 526 and passes through the ¼ λ retardation wave-plate for the second time it becomes polarized in the P-plane, perpendicular to the original polarization plane. This causes the reflected beam to be almost totally transmitted by the beam splitter 522 to the first lens assembly 520 and then through the second beam splitter 518 onto the surface of the SLM device 516. The SLM rotates the polarization of the reflected beam by 90 degrees and thus, the beam is almost totally reflected from the second beam splitter 518.

Although the invention is illustrated with a particular optical arrangement operating in a reflective filtering mode in the focal plane with a Liquid Crystal on Silicon (LCOS) or micro-mirror SLM device, this is only one possibility. Another feasible implementation is in a transmissive mode of operation where the focal plane is equipped with a transmissive SLM of comparable properties.

The targeted instrument performance is only possible through the use of an electrically programmable SLM device that meets very demanding performance requirements. Such a device has only recently become available and the present invention presents its first application in the domain of interest.

In a specific embodiment of the invention, the programmable optical Fourier filter uses a Vertically Aligned Nematic (VAN) homeotropic Liquid Crystal SLM or Electrically Controlled Birefringence (ECB) Mode Liquid Crystal on Silicon (LCOS) reflective SLM device. Suitable VAN homeotropic Liquid Crystal SLM devices are manufactured by: Philips Electronics of the Netherlands, having a U.S. office at Briarcliff Manor, N.Y.; Microdisplay of San Pablo, Calif. U.S.A.; TDMC of Chunan, Miaoli, Taiwan; and the ILA Devices Section of the JVC Components & Device Company, Japan. ECB Mode LCOS reflective SLM devices are manufactured by Hitachi Corporation of Japan, having a U.S. office at Norcross, Ga. However, a reflective or transmissive device of comparable properties can also be employed, if it satisfies the following specifications.

The SLM device employed provides a contrast ratio sufficient to effectively block periodic signal components while still passing non-periodic signal components of the dimensions of primary interest. Accordingly, a contrast ratio exceeding 500:1 is preferred. For embodiments specifying inferior defect detection limits (larger defects detectable) lower contrast ratios can be utilized. In practice, a contrast ration of about 300:1 is required for an instrument according to the invention to perform properly, although it is within the spirit and scope of the invention to employ a contrast ratio as low as 100:1 if other performance requirements are met and detection limits are relaxed. Moreover, the preferred device preserves this high contrast ratio across a wide range of incidence angles ($\geq \pm 14$ degrees). This range should at least support what is determined by the specific telecentric lens design. These properties permit a very high suppression of the periodic components in the original signal across the entire large FOV of the lens system. Hence, the illumination intensity can be significantly increased while the periodic components in the signal are kept below the image capture device random noise level. This leads to high defect SNR and permits the use of very straightforward digital signal processing techniques, such as simple thresholding, to achieve defect detection and sizing.

It is important that the SLM device provide a fill factor high enough to suppress parasitic diffraction due to the SLM itself. The fill factor is the ratio (in percentage) of the SLM's electrically controllable surface area to its entire optically usable surface area. Since the inter-pixel spaces within the SLM act as a diffraction grating, a large fill factor value (approaching 100%) minimizes parasitic diffraction due to the SLM itself. Hence, a large fill factor, preferably $\geq 90\%$ further improves the defect SNR achievable.

Optical uniformity and wavefront distortion across the surface of the SLM is another important property of the preferred SLM. The invention works more efficiently if the distortion does not exceed one $\lambda$ over 20 mm. This results in non-distorted final images, which facilitates defect localization as well as prevents deterioration of defect SNR due to corruption of the light amplitude and phase.

The SLM used in accordance with the invention preferably has a high overall light throughput. The invention works more efficiently with at least 80% light reflectivity or transmissivity. This high light throughput makes the use of single-mode semiconductor lasers practical.

Another property of the employed SLM is its favorable size with adequate resolution. Having a 19.45 mm×14.59 mm active area with 1024×768 active pixels, the device sufficiently matches the lens design (providing a 20 mm×20 mm focal plane size). The resolution makes it possible to selectively attenuate individual peaks in the Fourier spectrum with minimum impairment of the system light throughput. The SLM physical size, while it provides the required resolution, also facilitates compact optical system design such that multiple channel instrument operation is feasible. The latter is one of the features that assists in meeting the requirements of the application domain considered. An SLM device with smaller size and larger number of active pixels would improve the operation of the present instrument and can be used provided it meets the remaining specifications.

The demanding defect detection limits required by the application domain of interest are unattainable without an optimal filter implemented in the lens focal plane. Apart from an electrically programmable SLM device of required specification, this system works more efficiently with an algorithm to determine the optimal masking pattern to be programmed into the SLM device. The filter optimization should take into account the following factors:

The filter pattern displayed on the SLM device should be sufficient to suppress the periodic components of the signal as much as practical while passing as much energy as possible from non-periodic defects, hence resulting in a high defect SNR.

Preferably the filter should be robust against: surface deviations from flatness, such as article tilt or curvature; unavoidable small rotations of the article in the object plane; and semiconductor laser wavelength drift.

Figure 6:
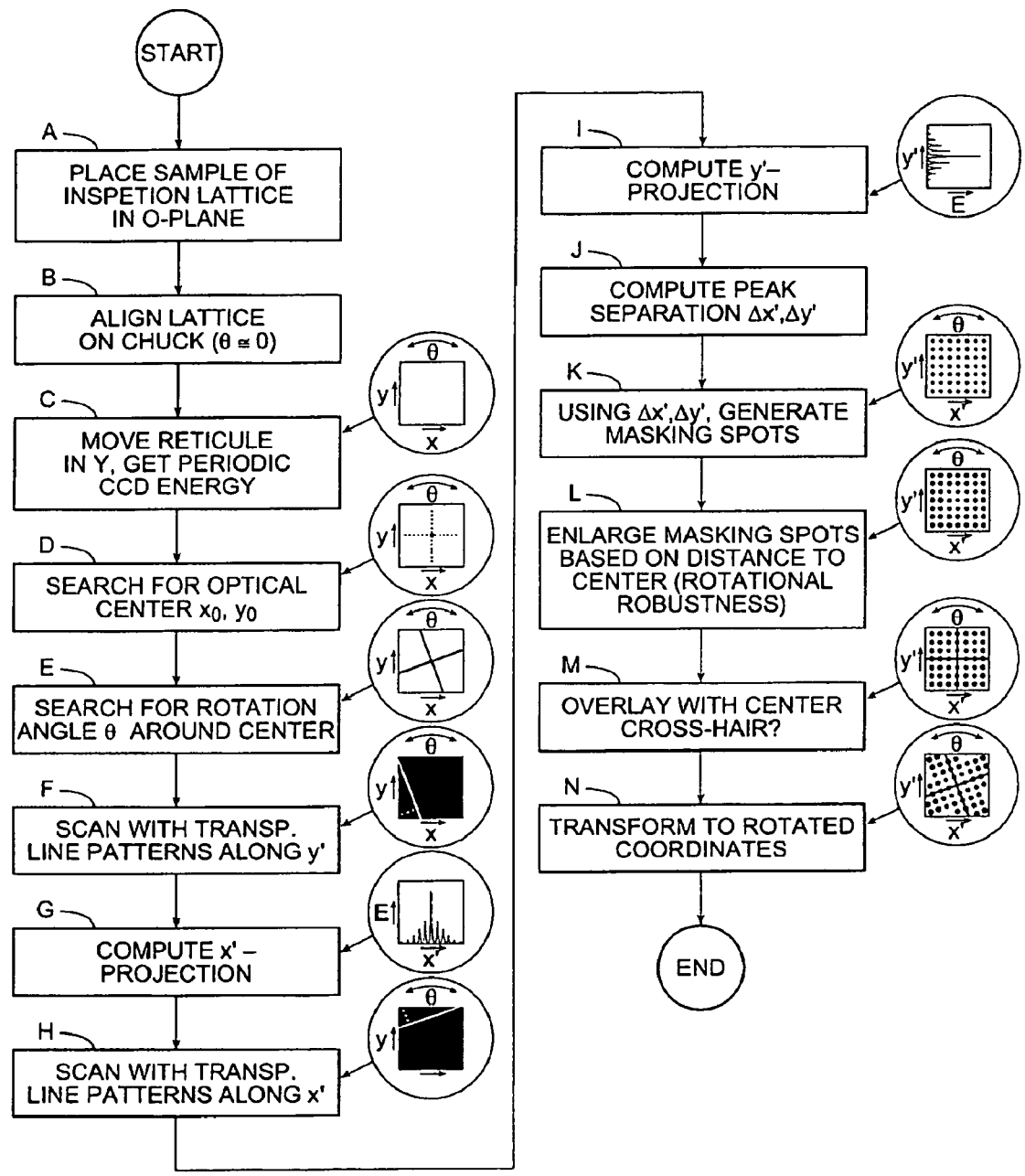
FIG. 6 is a flow chart of an algorithm using the SLM and CCD image capture device to determine the correct filtering pattern.

In a specific embodiment, the algorithm according to the invention interactively uses the SLM, the CCD image capture device, and a feedback network to determine the optimized filtering pattern. The procedure is illustrated in FIG. 6 in flowchart form. Note that the filtering pattern diagrams are not to scale and the rotational values are exaggerated for illustration purposes.

In order to derive and optimize the filtering pattern, a region of the substrate with the reference periodic pattern is placed under the field of view of the system (Step A). The substrate is mechanically aligned to the best possible extent, such as will be done during the actual inspection of the subsequent substrates for defects (Step B). Although a rotational correspondence to the alignment of the SLM is desirable for improved efficiency of the filter, such a correspondence is not necessary since the algorithm has a provision for compensating for any rotational misalignment. Subsequently, the substrate is moved along the web direction (along the direction of scanning of the line scan camera) so that across the web (perpendicular to the scanning direction of the line scan camera) a periodic region is observed on the CCD image capture device (Step C). The SLM device is kept completely reflective during this operation.

The following step is to determine the center axis of the optical system on the SLM (Step D). Again, although a prior mechanical alignment is desirable to have the main optical axis in close vicinity to the SLM center, only a coarse alignment is required. This step will compensate for any center misalignment of the SLM device. For this purpose, a single SLM pixel center spot is displayed on the SLM and the corresponding CCD energy is monitored while this center spot is made to scan the center area of the Fourier image. The spot location leading to the minimum energy in the final image plane corresponds to the optical center. This procedure makes use of the properties of the focal plane image such that the optical center will correspond to the DC component of the signal and hence the maximum energy peak. Accordingly, when this center spot is suppressed by the SLM spot mask, a significant energy drop will be observed in the final image plane.

Following center optimization, a rotational alignment verification is performed (Step E). This step is necessary to compensate for any rotational misalignment of the SLM around the optical axis with respect to the reference pattern alignment. It can also be used for the inspection of individual substrates in case no assumption is made about the rotational alignment of the pattern on a particular substrate. For this step, the SLM device is made reflective except a one pixel thin cross-hair mask pattern which is displayed on the SLM and centered with respect to the Fourier image. Accordingly, the center of the cross-hair pattern corresponds to the center location determined in step D. The CCD energy in the final image plane is monitored while the cross-hair pattern is rotated around its center axis. The angular search space is often limited to a small range wherein any misalignments are expected to lie. The angle of rotation leading to the minimum CCD energy is assumed to correspond to the correct value.

The subsequent two steps correspond to the determination of the interference peak separations along the rotationally compensated x' and y' axis. For example, to determine the peak separation along the x'-axis, the SLM is totally masked except for a thin reflective "window" along the y'-axis (Step F). This line shaped "window" is propagated along the x'-axis and an energy projection (Step G) is computed using the CCD energy for each window position. This profile is either thresholded or used in conjunction with a peak determination procedure to obtain the interference peak separation for the x'-axis. A very similar procedure is repeated to determine the y'-axis peak separation (Steps H and I). For some LCD lattices, the periodicity corresponding to the larger cell dimension may cause interference peaks which are too close to one another on the focal plane. Alternatively for this case, the described procedure may be used on the axis with the larger peak separation and prior knowledge of cell dimensions may be used to derive the value for the other axis.

After these steps, a useable filter is obtained (Step K) and can be applied in conjunction with the determined rotational alignment (Step N). The algorithm of the present invention may incorporate optional features, which may be used to further optimize the filter behavior for certain cases. One example is a rotational robustness feature (Step L), which can be used to increase filter robustness against small rotational misalignments of the pattern on the substrate, which may happen from sample to sample. It may especially improve system performance when such inter sample variations occur and when there is not enough time available to perform filter re-optimization. For this step, the base masking spot size is increased toward the SLM periphery in proportion to the distance from the pattern center. This is due to the fact that the displacement of individual interference peaks corresponding to a fixed rotation increases in value as one moves away from the center of rotation. Another example is use of a center cross-hair pattern to suppress the main axis of the interference pattern. It is understood that the shape and size of the mask provides selective suppression of the spectral peaks in the Fourier plane to provide improved selective spectral suppression.

The use of OFF with the specific lens design, illuminator, SLM device, and filtering algorithm achieves a very high defect SNR in the optically filtered final image captured by the CCD image capture device. In the digitized image, the periodic lattice residue is suppressed down to the sensor random noise level while all non-periodic defects stand out from a dark background. The defect intensity correlates to their size and contrast.

Hence, a very simple and fast digital processing of the captured image in the form of a fixed threshold, placed just above the noise level, can be utilized. This results in a simple and fast hardware implementation in the form of field programmable gate array (FPGA) firmware. The fast image processing is critical to meet the tact time requirements of the application domain. As a result of this processing, the presence, location, and size of the defects are obtained.

This is illustrated in FIG. 4C and FIG. 4D, where cross-sectional views of a low contrast "dark" defect 410 are shown. The defect contrast is significantly improved and the filtered defect signal rises over a uniformly low background 416. Since the optical Fourier filter has also eliminated the low spatial frequency background fluctuations, a simple fixed threshold 414 is sufficient to perform defect detection and thus, cumbersome techniques of background correction or differential thresholding are not necessary.

The invention operates more efficiently and the validity of the applied optical filter is increased when mechanically and/or pneumatically constrained means are incorporated to move the inspected flat media (or the optical system), so that the deviation from flatness is less than 10 μm over a media span of 20 mm. Also, the rotational instability of the media while in motion should not exceed ±0.5 degrees.

Figure 7:
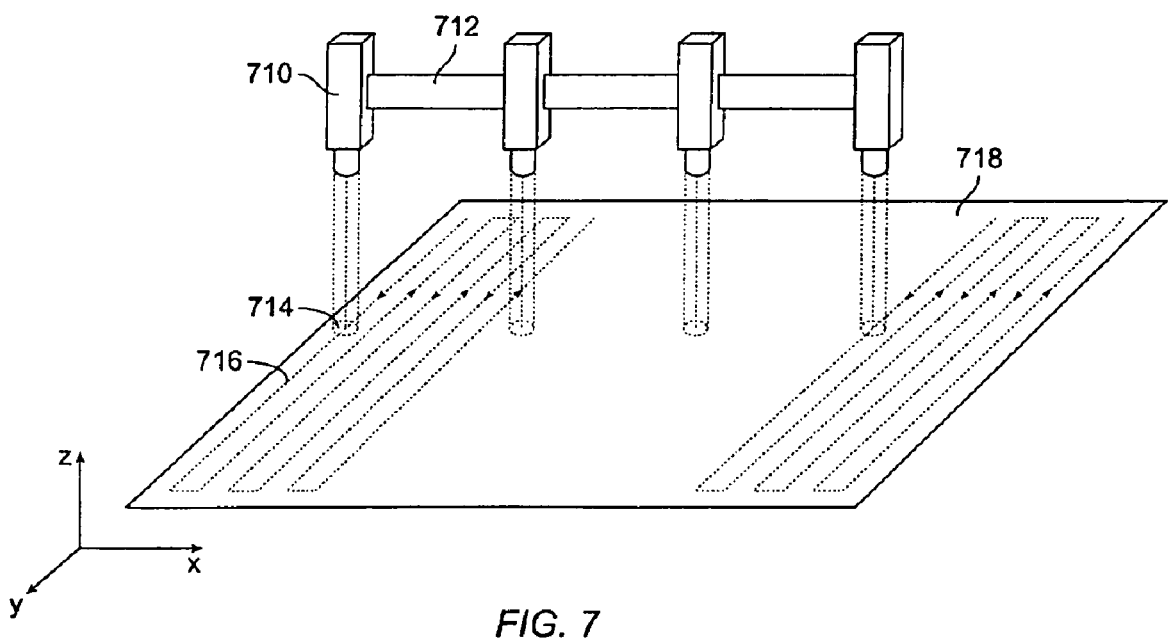
FIG. 7 is a schematic diagram of a four channel system of the present invention.

The short tact time requirements of some application domains of interest are not realizable even with single channel, wide FOV optics. Therefore, the present invention operates more efficiently when multiple identical instances of wide FOV imaging channels incorporating OFF are used to concurrently scan multiple FOVs across the web direction in multiple passes. Such a configuration is illustrated in FIG. 7 for a hypothetical 4 channel system. The channels 710, incorporating all optical filtering, illumination and optics, are connected together through a very rigid and high precision gantry 712. The entire area of the substrate 718 is covered in multiple passes 716 with either the gantry moving over substrate, or the substrate moving under the gantry.

One embodiment of the instrument covers a 2100 mm×1800 mm scan area with 10 imaging channels and 6 detection passes in 60 seconds tact time, achieving a 100% inspection of the surface with a low contrast defect detection limit of 3.5 μm.

Figure 8A:
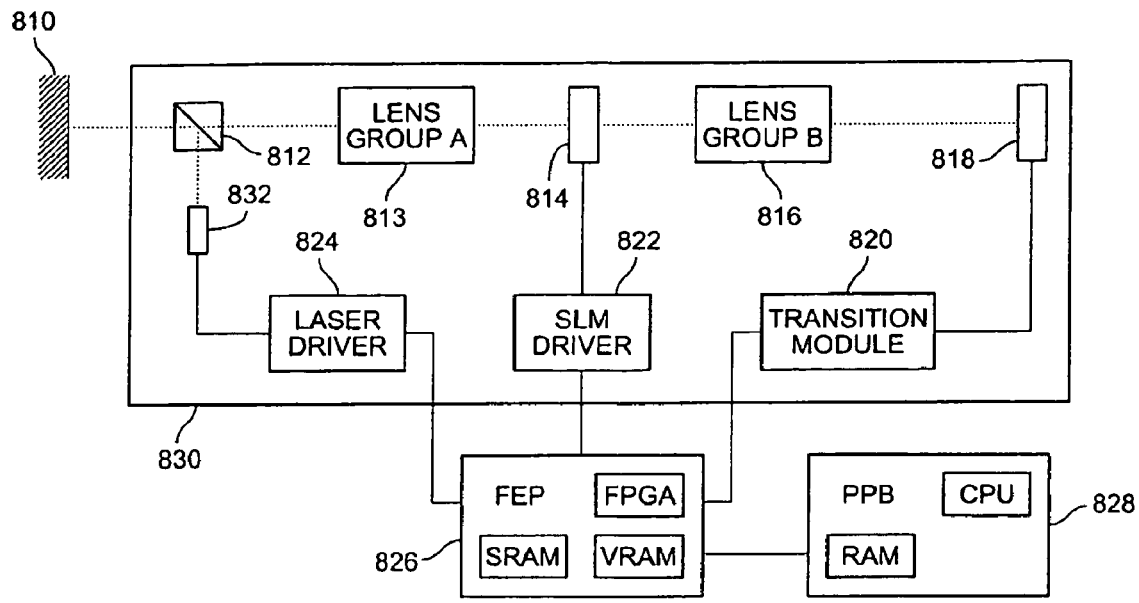
FIG. 8A is a functional diagram of a single imaging/optical filtering channel.
Figure 8B:
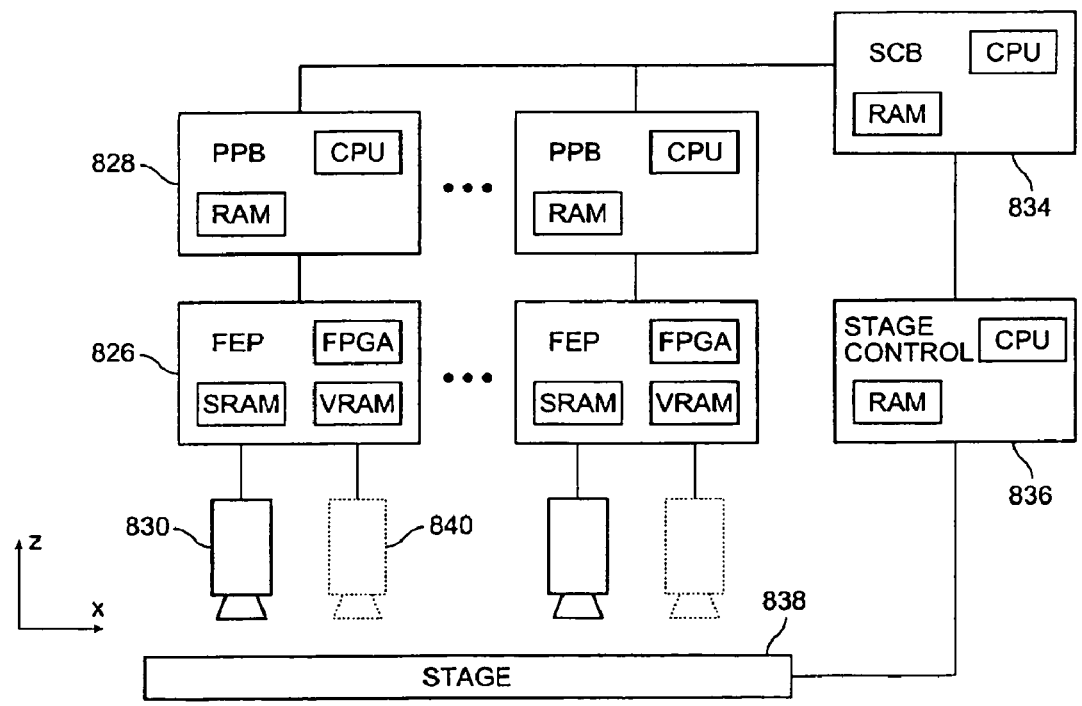
FIG. 8B is a functional diagram for multiple channel operation.

FIG. 8A illustrates the functional system components for a single imaging/optical filtering channel. FIG. 8B illustrates the functional system components for multiple channel operation. The optical path includes the object plane 810, the illumination beam splitter 812, the first lens group 813, the SLM 814, the second lens group 816 and the image capture device 818. In FIG. 8A, each individual channel is controlled by a Front End Processor (FEP) 826. This is a processor board composed of one or more FPGAs associated with Synchronous Dynamic Random Access Memory (SDRAM) and Video RAM (VRAM). The FEP controls the laser illumination 832 through a laser driver module 824, the SLM 814 through an SLM driver module 822, and the CCD image capture device 818 through a transition module 820. The FEP in turn is controlled by slower but more flexible general purpose computation hardware 828 acting as a Peripheral Processor Board (PPB) encompassing a general purpose central processing unit (CPU), memory, and permanent storage device. As seen in FIG. 8B, each FEP-PPB pair can be configured to control more than one camera channel 830 and 840 and multiple such pairs are used to perform multiple channel operation. Defect detection, preliminary classification, and image collection is performed at FEP-PPB level, while the System Control Board (SCB) coordinates data flow from multiple channels and provides the control signals to the X-Y-Z stage 838 through a specific computer controller board 836. The stage 838 transports and constrains the media to be inspected to comply with the flatness and motion requirements of the imaging system. Alternatively, the imaging channels, instead of the media, may be moved along some particular axis. An example could be the movement of cameras along the z-axis for automatic focusing.

The invention has been explained with reference to specific embodiments. Other embodiments will be evident to those of ordinary skill in the art. It is therefore not intended that the invention be limited, except as indicated by the appended claims.

What is claimed is:

1. A system for inspecting a planar object having a periodic structure to indicate defects in said planar object comprising:

a plurality of imaging channel heads, each imaging channel head comprising:

an optical Fourier filter implemented by an electrically programmable spatial light modulator, said spatial light modulator being reconfigurable and having a contrast ratio sufficient to suppress periodic components of a transformed image of said planar object to less than optical sensor noise levels of a spatial image detector;

a lens assembly of a sufficiently large field of view to interact with said spatial light modulator;

a laser illumination system disposed to illuminate the planar object with coherent illumination and to produce optical energy intensity sufficient to saturate the spatial image detector absent the optical Fourier filter; and a feedback system associated with each said imaging channel head and responsive to output of the spatial image detector and operative according to an algorithm to computationally control the electrically programmable spatial light modulator to invoke an aligned filtering pattern sufficient to suppress the periodic components of the transformed image.

2. The system according to claim 1 wherein the electrically programmable spatial light modulator is characterized by:

a contrast ratio of at least 500:1 over a range of incidence angles of at least ±14 degrees;

a fill factor of at least 90%;

optical nonuniformity and wavefront distortion across the surface of the spatial light modulator of less than one wavelength over 20 mm;

optical energy throughput of at least 80%; and an active area of less than 20 mm×20 mm; and at least 1024×768 active pixels within said active area.

3. The system according to claim 1 wherein the lens assembly further comprises:

a telecentric lens set comprising a plurality of lenses wherein:

a first lens is disposed to produce infinite conjugates; and a second lens is disposed to satisfy lens assembly constraints.

4. The system according to claim 1 wherein the laser illumination system further comprises:

a single-mode semiconductor laser operating in a single spatial mode to produce a beam along a path;

a plurality of quarter-wave plates disposed in said path; and polarizing beamsplitters disposed in said path, said polarizing beamsplitters increasing light throughput by a factor of at least 16 times relative to non-polarizing beamsplitters.

5. The system according to claim 1 further including a physical translator element to constrain distance between the planar object and each one of the plurality of imaging channels to vary no more than 10 m over a translation of 20 mm of the imaging channel in a plane parallel to the planar object.

6. The system according to claim 1 wherein the electrically programmable spatial light modulator is operative to vary spot size for decreasing sensitivity to rotational misalignment.

7. The system according to claim 6 wherein the spot size variation is implemented by variation in base masking spot size in proportion to the distance from pattern center.

8. The system according to claim 6 wherein said electrically programmable spatial light modulator comprises a rotationally alignable mask pattern in form of a cross-hair set.

* * * * *